(12) United States Patent
Hara et al.

(10) Patent No.: US 10,336,783 B2
(45) Date of Patent: Jul. 2, 2019

(54) SOLID CATALYST FOR HYDRIDE ISOMERIZATION REACTION IN AN AQUEOUS MEDIUM

(71) Applicant: JAPAN SCIENCE AND TECHNOLOGY AGENCY, Kawaguchi-shi (JP)

(72) Inventors: Michikazu Hara, Yokohama (JP); Kiyotaka Nakajima, Yokohama (JP); Daiki Takeda, Yokohama (JP)

(73) Assignee: JAPAN SCIENCE AND TECHNOLOGY AGENCY, Kawaguchi-shi (JP)

( * ) Notice: Subject to any disclaimer, the term of this patent is extended or adjusted under 35 U.S.C. 154(b) by 0 days.

(21) Appl. No.: 15/124,939

(22) PCT Filed: Mar. 10, 2015

(86) PCT No.: PCT/JP2015/057015
§ 371 (c)(1),
(2) Date: Sep. 9, 2016

(87) PCT Pub. No.: WO2015/137339
PCT Pub. Date: Sep. 17, 2015

(65) Prior Publication Data
US 2017/0022238 A1    Jan. 26, 2017

(30) Foreign Application Priority Data
Mar. 11, 2014    (JP) .................. 2014-047270

(51) Int. Cl.
| | | |
|---|---|---|
| *C07H 3/02* | (2006.01) | |
| *B01J 27/18* | (2006.01) | |
| *B01J 37/28* | (2006.01) | |
| *B01J 27/16* | (2006.01) | |
| *B01J 21/04* | (2006.01) | |
| *B01J 23/08* | (2006.01) | |
| *B01J 35/00* | (2006.01) | |
| *B01J 35/10* | (2006.01) | |
| *C07H 1/00* | (2006.01) | |

(52) U.S. Cl.
CPC .............. *C07H 3/02* (2013.01); *B01J 21/04* (2013.01); *B01J 23/08* (2013.01); *B01J 27/16* (2013.01); *B01J 27/1811* (2013.01); *B01J 35/002* (2013.01); *B01J 35/1014* (2013.01); *B01J 35/1019* (2013.01); *B01J 37/28* (2013.01); *C07H 1/00* (2013.01)

(58) Field of Classification Search
CPC ...................................................... C07H 3/02
See application file for complete search history.

(56) References Cited

U.S. PATENT DOCUMENTS

| | | | | |
|---|---|---|---|---|
| 5,139,759 A | * | 8/1992 | Cannan | C01B 39/40 423/709 |
| 5,985,790 A | * | 11/1999 | Moskovitz | B01J 20/06 423/604 |
| 2006/0024226 A1 | * | 2/2006 | Park | B01D 53/8659 423/240 S |
| 2008/0216391 A1 | | 9/2008 | Cortright et al. | |
| 2011/0207923 A1 | * | 8/2011 | Moliner-Marin | C07D 307/58 536/125 |
| 2013/0150595 A1 | * | 6/2013 | Dumesic | C07D 307/48 549/488 |

FOREIGN PATENT DOCUMENTS

| | | |
|---|---|---|
| CN | 1087894 A | 6/1994 |
| CN | 101119956 A | 2/2008 |
| JP | 2007-196174 A | 8/2007 |
| JP | 2013-6142 A | 1/2013 |
| JP | 2013-517288 A | 5/2013 |
| WO | WO 97/47380 A1 | 12/1997 |
| WO | WO 99/58238 A1 | 11/1999 |
| WO | WO 2011/036862 A1 | 3/2011 |
| WO | 2012/108472 A1 | 8/2012 |
| WO | 2013/030132 A1 | 3/2013 |

OTHER PUBLICATIONS

International Search Report dated Jun. 16, 2015 in PCT/JP2015/057015 filed Mar. 10, 2015.
Manuel Moliner, et al., "Tin-containing zeolites are highly active catalysts for the isomerization of glucose in water", PNAS, vol. 107, No. 14, Apr. 6, 2010, pp. 6164-6168.
V.V. Ordomsky, et al., "Glucose dehydration to 5-hydroxymethylfurfural over phosphate catalysts", Journal of Catalysis, vol. 300, 2013, pp. 37-46.
Extended European Search Report dated Oct. 13, 2017 in Patent Application No. 15762249.9.
Combined Office Action and Search Report dated Dec. 28, 2017 in Chinese Patent Application No. 201580012750.3 (with English translation of categories of cited documents), 6 pages.

* cited by examiner

*Primary Examiner* — Douglas B Call
(74) *Attorney, Agent, or Firm* — Oblon, McClelland, Maier & Neustadt, L.L.P.

(57) ABSTRACT

A novel catalyst capable of selectively catalyzing conversion from glucose to fructose in water or in an aqueous solution is provided. The catalyst is a solid catalyst for a hydride isomerization reaction from glucose to fructose performed in water or in an aqueous solution, comprising a group 13 element oxide whose surface has been subjected to a phosphoric acid treatment.

8 Claims, 7 Drawing Sheets

SOLID CATALYST FOR HYDRIDE ISOMERIZATION REACTION IN AN AQUEOUS MEDIUM

FIELD OF THE INVENTION

The present invention relates to a solid catalyst working in an aqueous medium to catalyze a hydride isomerization reaction of glucose, and a use thereof.

BACKGROUND OF THE INVENTION

In recent years, a chemical reaction performed in water or in an aqueous solution attracts attention because it is superior, in an environmental load, safety and the like, to a reaction performed in an organic solvent, which has been widely performed. Meanwhile, a Lewis acid catalyst is widely applied to Friedel-Crafts alkylation/acylation reactions, various coupling reactions, polycondensation, dislocation, isomerization, dehydration reactions, and the like, and most of these reactions are performed in an organic solvent, and hence, there is a demand for a Lewis acid catalyst which does not decompose but works in water.

A biomass is a renewable resource, and is regarded as a promising novel carbon source to replace crude oil. Above all, glucose is produced from a variety of plant materials, and it is known that 5-hydroxymethylfurfral (HMF) obtained through dehydration of glucose can be a raw material of useful chemical substances such as furfuryl alcohol and tetrahydrofuran. As a reaction for producing HMF from glucose, a method in which glucose is converted into fructose through a hydride transfer reaction, and the fructose is dehydrated to produce HMF is widely employed. In this reaction, a reaction using, as a catalyst, phosphoric acid/$TiO_2$ or phosphoric acid/$Nb_2O_5$ is known as a method for producing HMF from a glucose aqueous solution, but such a metal oxide is expensive and hence is industrially difficult to use. Besides, it is reported that Sn-containing β-zeolite is effectively used for producing fructose from a glucose aqueous solution (Non Patent Literature 1). Furthermore, it is reported that HMF can be produced from glucose by using a phosphoric acid compound in which phosphoric acid is incorporated in a skeleton-forming component such as aluminum phosphate (Non Patent Literature 2).

CITATION LIST

Non Patent Literature

[Non Patent Literature 1] PNAS, 107, 6164-6168 (2010)
[Non Patent Literature 2] Journal of Catalysis, 300 (2013), 37-46

SUMMARY OF THE INVENTION

Technical Problem to be Solved by the Invention

The reaction using the Sn-containing β-zeolite causes, however, a large number of side reactions, and not only fructose and HMF but also a large number of products are generated, and hence this method is not industrially applicable. Besides, Sn has a safety problem, and cannot be used for producing fructose to be used in food.

Furthermore, aluminum phosphate is low not only in catalytic activity but also in fructose selectivity, and hence is difficult to apply as an industrial catalyst.

Accordingly, an object of the present invention is to provide a novel catalyst capable of selectively catalyzing, in water or in an aqueous solution, a desired hydride isomerization reaction from glucose to fructose.

Solution to Problem

As described above, in the process of producing HMF from glucose, the conversion reaction from fructose to HMF satisfactorily proceeds in a Brönsted acid, and therefore, if the conversion reaction from glucose to fructose can be selectively performed, the process can be industrially advantageous as a whole, and the fructose can be applied also to food such as a sweetener. Therefore, the present inventors have studied solid catalysts capable of causing conversion from glucose to fructose to selectively proceed in an aqueous medium, and have found that a catalyst obtained by treating, with phosphoric acid, a surface of a group 13 element oxide such as aluminum oxide causes a hydride isomerization reaction from glucose to fructose to selectively proceed in an aqueous medium, and thus, the present invention was accomplished.

Specifically, the present invention provides the following [1] to [5]:

[1] A solid catalyst for a hydride isomerization reaction from glucose to fructose performed in water or in an aqueous solution, comprising a group 13 element oxide whose surface has been subjected to a phosphoric acid treatment.

[2] The solid catalyst according to [1], in which the group 13 element oxide is selected from the group consisting of aluminum oxide, gallium oxide, indium oxide and thallium oxide.

[3] The solid catalyst according to [1] or [2], in which the phosphoric acid treatment is performed by treating the group 13 element oxide in a phosphoric acid aqueous solution at 50° C. or lower.

[4] The solid catalyst according to any one of [1] to [3], in which a Lewis acid amount in the group 13 element oxide whose surface has been subjected to a phosphoric acid treatment is kept, in a state where the surface is hydrated, at 80% or more of a Lewis acid amount in a dehydrated surface portion of the group 13 element oxide not subjected to the phosphoric acid treatment.

[5] A method for producing fructose, comprising allowing the catalyst according to any one of [1] to [4] to work on glucose in water or in an aqueous solution.

Effect of Invention

A catalyst of the present invention is useful as a solid catalyst having high selectivity for a hydride isomerization reaction from glucose to fructose performed in water or in an aqueous solution. According to a method of the present invention, fructose can be obtained with high selectivity from glucose through a reaction performed in water or in an aqueous solution.

DESCRIPTION OF EMBODIMENT

Figure 1:
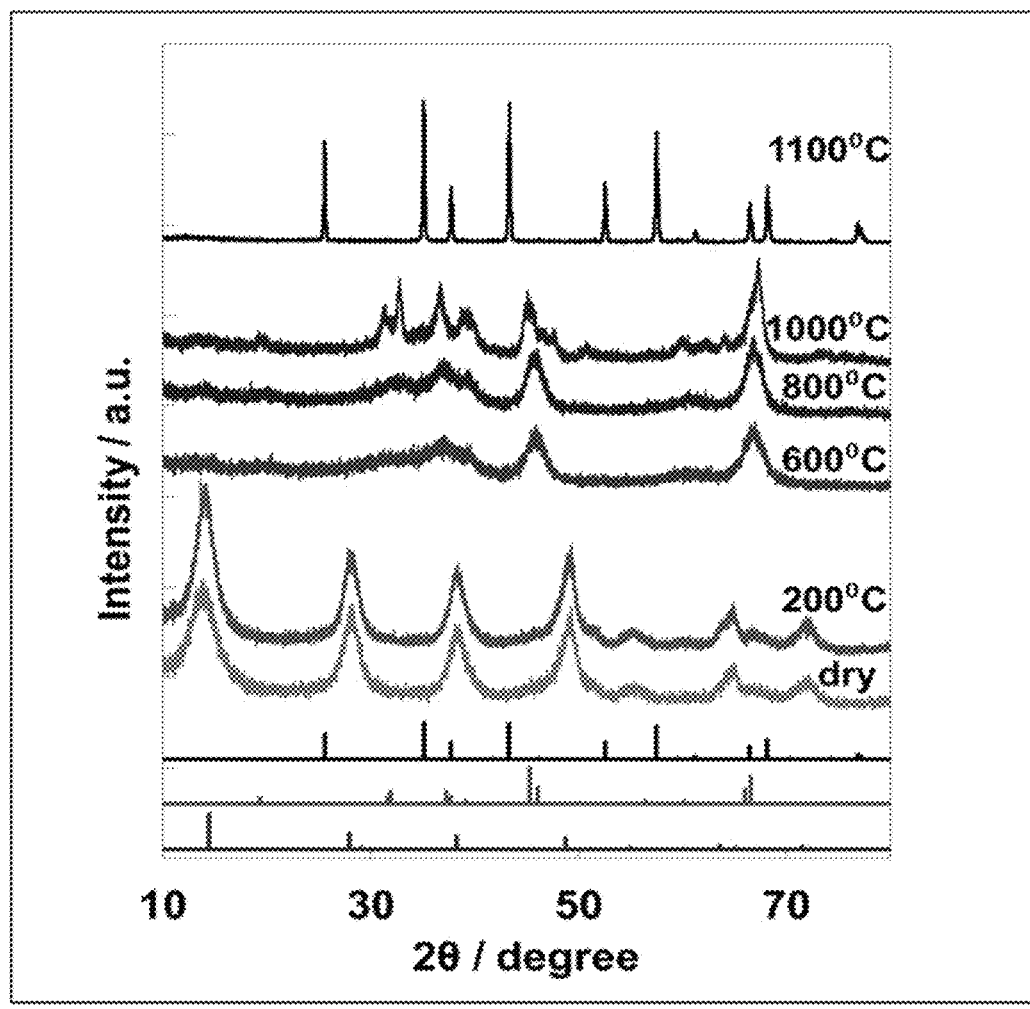
FIG. 1 illustrates XRD spectra of aluminum oxides obtained in Reference Example 1.

A catalyst of the present invention is a solid catalyst for a hydride isomerization reaction from glucose to fructose performed in water or in an aqueous solution, comprising a group 13 element oxide whose surface have been subjected to a phosphoric acid treatment.

Examples of the group 13 element oxide include aluminum oxide, gallium oxide, indium oxide and thallium oxide. Examples of the aluminum oxide include α-alumina, β-alumina, γ-alumina, δ-alumina, θ-alumina and boehmite, and γ-alumina is particularly preferred. Examples of the gallium oxide include α-$Ga_2O_3$, β-$Ga_2O_3$, γ-$Ga_2O_3$, δ-$Ga_2O_3$ and ε-$Ga_2O_3$, and β-$Ga_2O_3$ is more preferred. The indium oxide may be any $In_2O_3$, and the thallium oxide may be any $Tl_2O_3$.

Among these group 13 element oxides, aluminum oxide is preferred from the viewpoint of easy availability and the like.

As the phosphoric acid treatment for the surface of the group 13 element oxide, the group 13 element oxide may be treated with, for example, a phosphoric acid aqueous solution of 50° C. or lower. Specifically, the group 13 element oxide may be stirred in a phosphoric acid aqueous solution of 50° C. or lower. If the phosphoric acid treatment is performed at a high temperature, phosphorylation proceeds not only in a surface portion but also to the inside of the group 13 element oxide, which is unpreferable because its function as a Lewis acid catalyst is lowered. Here, it can be confirmed through solid NMR whether the surface portion alone is phosphorylated.

A concentration of the phosphoric acid aqueous solution to be used may be 1 mM or more, is preferably 1 mM to 100 mM, and more preferably 10 mM to 100 mM. A molar ratio between the group 13 element oxide and phosphoric acid to be used is not especially limited as long as a part of the surface of the group 13 element oxide can be phosphorylated, and 0.0001 mol or more of phosphoric acid may be used per mol of the group 13 element oxide, and 0.0001 to 1 mol of phosphoric acid is more preferably used. A treatment temperature is preferably 50° C. or lower, more preferably 0 to 50° C., and is economically and further preferably 10 to 40° C. Besides, a treatment time for stirring may be 5 minutes or more, preferably about 5 minutes to 48 hours, and more preferably 15 minutes to 24 hours.

After the phosphoric acid treatment, the group 13 element oxide having the phosphoric acid-treated surface is separated from the mixture through filtration or the like.

Through the above-described phosphoric acid treatment of the group 13 element oxide, the phosphoric acid is immobilized on the surface of the group 13 element oxide. This immobilization is probably caused through bond of the phosphoric acid to the surface of the group 13 element oxide, and the phosphoric acid is probably bonded in the form of —OP(=O)(OH)$_2$. This bond can be checked through the solid NMR. Besides, the phosphoric acid treatment does not proceed to the inside of the group 13 element oxide. Incidentally, there is no need to subject the whole surface of the group 13 element oxide to the phosphoric acid treatment, but 0.00001 mol % or more of phosphoric acid may be immobilized on the group 13 element oxide, and preferably 0.0001 to 0.003 mol % is immobilized, and more preferably 0.0003 to 0.0015 mol % of phosphoric acid is immobilized.

In the group 13 element oxide having the phosphorylated surface, it is preferable that the surface is phosphorylated and that a sufficient Lewis acid amount is kept in a surface portion. If a sufficient Lewis acid amount is kept in the surface portion and the surface is phosphorylated, a reaction from glucose to fructose selectively proceeds, and a side reaction can be inhibited. The Lewis acid amount in the surface portion of the present solid catalyst is, in a state where the surface is hydrated, kept at preferably 80% or more and more preferably 85% or more of a Lewis acid amount in a dehydrated surface portion of the group 13 element oxide not subjected to the phosphoric acid treatment. The Lewis acid amount is kept at more preferably 80 to 95% and further preferably 85 to 95%. Here, a Lewis acid amount can be measured based on an FTIR spectrum of a sample to which pyridine has been adsorbed.

Incidentally, in the group 13 element oxide having the phosphorylated surface, if the surface is hydrated, the Lewis acid amount is increased as compared with that in the dehydrated surface portion. This catalyst seems to excellently catalyze the hydride isomerization reaction in water or in an aqueous solution owing to this function.

A particle size of the group 13 element oxide having the phosphorylated surface is not especially limited, and is substantially the same as that of a particle of the group 13 element oxide used as a raw material, and for example, is preferably 0.1 to 100 μm, more preferably 1 to 100 μm, and further preferably 1 to 10 μm.

The group 13 element oxide having the phosphorylated surface is a solid, and after used as a catalyst, can be easily separated and collected from a reaction mixture by filtration or the like to be reused, and hence is useful as a solid catalyst.

The group 13 element oxide having the phosphorylated surface is useful as a solid catalyst for the hydride isomerization reaction from glucose to fructose performed in water or in an aqueous solution. Here, functionality in water or in an aqueous solution refers to a function to catalyze a reaction occurring in water or in an aqueous solution, and involves a reaction performed in an aqueous phase even if the reaction is caused in a mixed liquid of water and an organic solvent. The number of solid Lewis acid catalysts thus working in water or in an aqueous solution is small.

The catalyst of the present invention works as a Lewis acid catalyst for the hydride isomerization reaction from glucose to fructose.

If the catalyst of the present invention is allowed to work on glucose in water or in an aqueous solution, a side reaction is inhibited, the hydride isomerization reaction selectively proceeds, and fructose can be selectively produced.

A glucose concentration in the aqueous solution is not especially limited, and is preferably 0.1 to 50° by mass and more preferably 0.1 to 20% by mass. An amount of the present catalyst to be used is preferably 0.01 to 10 g, and more preferably 0.1 to 1 g per gram of the glucose. A reaction temperature is preferably 50 to 180° C., and more preferably 100 to 130° C. A reaction time is preferably 15 minutes to 24 hours, and more preferably 30 minutes to 10 hours.

When the catalyst of the present invention is used, fructose is selectively produced from glucose, a production rate of HMF is small, and in addition, the other complicated side reactions are inhibited. Selectivity in the production of fructose is remarkably excellent as compared with a case where the Sn-containing β-zeolite described in Non Patent Literature 1 or aluminum phosphate described in Non Patent Literature 2 is used.

EXAMPLES

The present invention will now be described in more detail with reference to examples.

Reference Example 1

To 30 g of aluminum isopropoxide (Al(O-i-Pr)$_3$), 300 mL of water was added, and the resultant was stirred at 80° C. for 5 hours, and then allowed to cool, and water was removed. The thus obtained precursor was calcined at 200 to 1,100° C. for 3 hours to obtain an aluminum oxide powder. An X-ray diffraction (XRD) spectrum of the thus obtained aluminum oxide is illustrated in FIG. 1, and a BET specific surface area and a crystalline phase thereof are shown in Table 1. In the table, Al-200 to Al-1100 refer to aluminum oxides respectively obtained at calcination temperatures of 200 to 1,100° C.

TABLE 1

| Catalyst | $S_{BET}$ (m$^2$/g) | Crystalline phase, XRD |
|---|---|---|
| Precursor | 345 | Boehmite Al$_2$O (OH) |
| Al-200 | 180 | Boehmite Al$_2$O (OH) |
| Al-600 | 132 | Y—Al$_2$O$_3$ |
| Al-800 | 102 | Y—Al$_2$O$_3$ |
| Al-1000 | 82 | Mixed crystal of δ-Al$_2$O$_3$ and θ-Al$_2$O$_3$ |
| Al-1100 | 3.2 | α-Al$_2$O$_3$ |

Reference Example 2

To 3 to 5 g of gallium isopropoxide (Ga(O-i-Pro)$_3$) or indium isopropoxide (In(O-i-Pro)$_3$), 75 to 100 mL of 2-propanol, 0.02 to 0.1 mL of acetic acid and 0.1 to 1.0 mL of water were added, and the resultant was stirred at 80° C. for 5 hours, filtrated and then dried. The thus obtained precursor was calcined at 200 to 1,000° C. for 3 hours to obtain Ga$_2$O$_3$ or In$_2$O$_3$. BET specific surface areas of the thus obtained products are shown in Table 2. In Table 2, a numerical value following Ga$_2$O$_3$ or In$_2$O$_3$ indicates the calcination temperature.

TABLE 2

| Catalyst | $S_{BET}$/m$^2$g$^{-1}$ |
|---|---|
| Ga$_2$O$_3$-Precursor | 218 |
| Ga$_2$O$_3$-200 | 193 |
| Ga$_2$O$_3$-300 | 206 |
| Ga$_2$O$_3$-500 | 135 |
| In$_2$O$_3$-Precursor | 182 |
| In$_2$O$_3$-200 | 180 |
| In$_2$O$_3$-400 | 66 |
| In$_2$O$_3$-600 | 40 |

Example 1

(1) Five g of the aluminum oxide produced in Reference Example 1 was stirred in 200 mL of a 0.1 M phosphoric acid aqueous solution at 25° C. for 24 hours. The resulting solution was filtrated, and a filtrate was dried to obtain 5.1 g of phosphoric acid-treated aluminum oxide. It was found, through X-ray fluorescence analysis, to contain 5% by mass of phosphoric acid.

Figure 2:
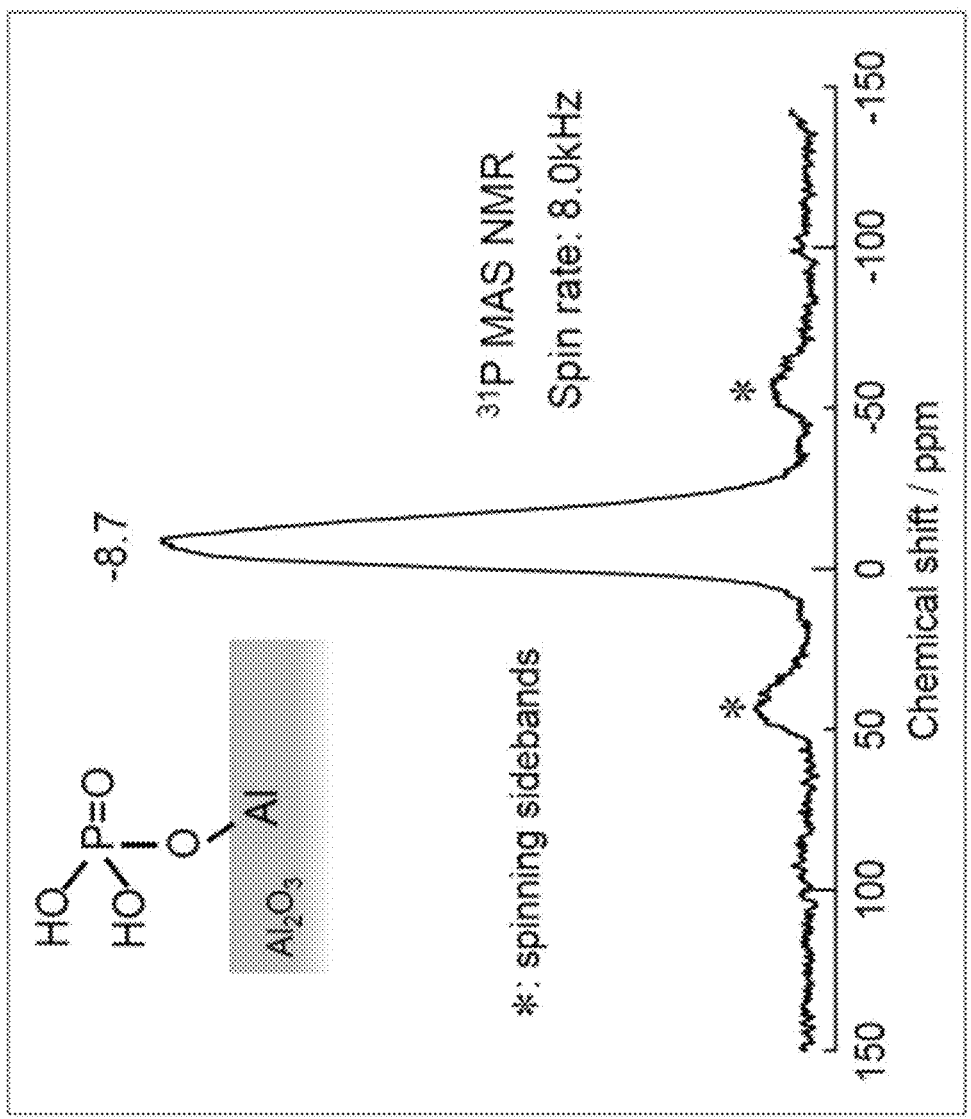
FIG. 2 illustrates a solid NMR ($^{31}$P MAS NMR) spectrum of phosphoric acid treated-aluminum oxide.

(2) Solid NMR ($^{31}$P MAS NMR) of the thus obtained phosphoric acid-treated aluminum oxide was measured (Spin rate: 8.0 KHz). As a result, it was confirmed, as illustrated in FIG. 2, that a surface portion alone of the aluminum oxide had a structure of Al—O—P(O)(OH)$_2$.

(3) Each of aluminum oxide and the phosphoric acid-treated aluminum oxide was subjected to a dehydration treatment (in an evacuated state, thermal dehydration at 300° C. for 1 hour) and a hydration treatment (exposure to saturated vapor at room temperature). Each of the thus obtained samples was measured for an FTIR spectrum through pyridine adsorption at room temperature followed by evacuation, and a proton acid amount (BAS) and a Lewis acid amount (LAS) were quantitatively determined. The results are illustrated in FIG. 3.

Figure 3:
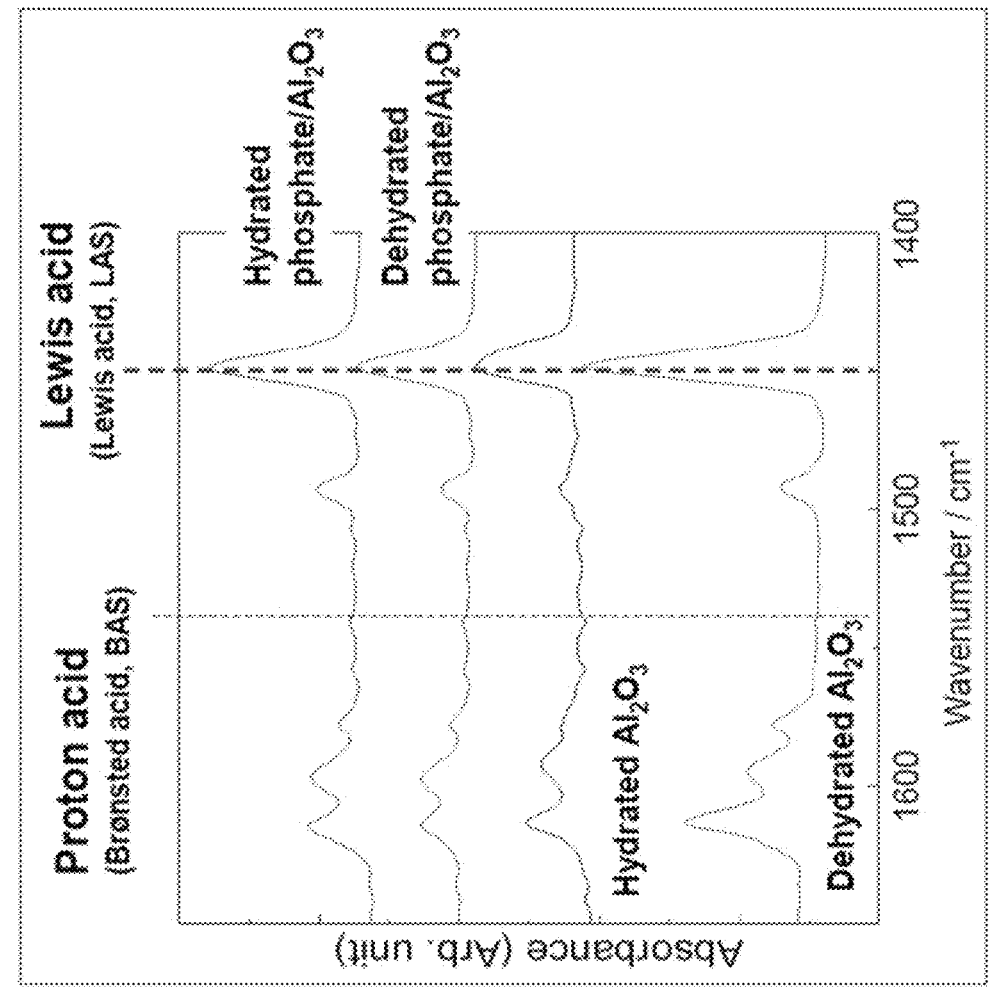
FIG. 3 illustrates FTIR spectra of aluminum oxide and phosphoric acid-treated aluminum oxide.

Lewis acid amounts calculated based on FIG. 3 are shown in Table 3.

TABLE 3

| | | Acid amount/mmol g$^{-1}$ | |
|---|---|---|---|
| | Surface state | BAS | LAS |
| Al$_2$O$_3$ (600° C.) | Dehydrated | — | 0.17 |
| | Hydrated | — | 0.11 |
| Phosphate/ Al$_2$O$_3$ | Dehydrated | — | 0.12 |
| | Hydrated | — | 0.15 |

It is understood from Table 3 that the Lewis acid amount in the phosphoric acid-treated aluminum oxide (hydrated) was kept at 88% of the acid amount in the dehydrated aluminum oxide. Besides, the Lewis acid amount of the phosphoric acid-treated aluminum oxide (hydrated) was larger than that of the phosphoric acid-treated aluminum oxide (dehydrated). In this manner, the Lewis acid amount of the hydrated phosphoric acid-treated aluminum oxide was sufficiently large, and hence, it was found that this phosphoric acid-treated aluminum is useful as a Lewis acid catalyst used in water or in an aqueous solution.

Example 2

Five g of the gallium oxide or indium oxide produced in Reference Example 2 was stirred in 200 mL of a 0.1 M phosphoric acid aqueous solution at 25° C. for 24 hours. The resulting solution was filtrated, and a filtrate was dried to obtain 4.5 g of phosphoric acid-treated gallium oxide or phosphoric acid-treated indium oxide.

Example 3

Figure 4:
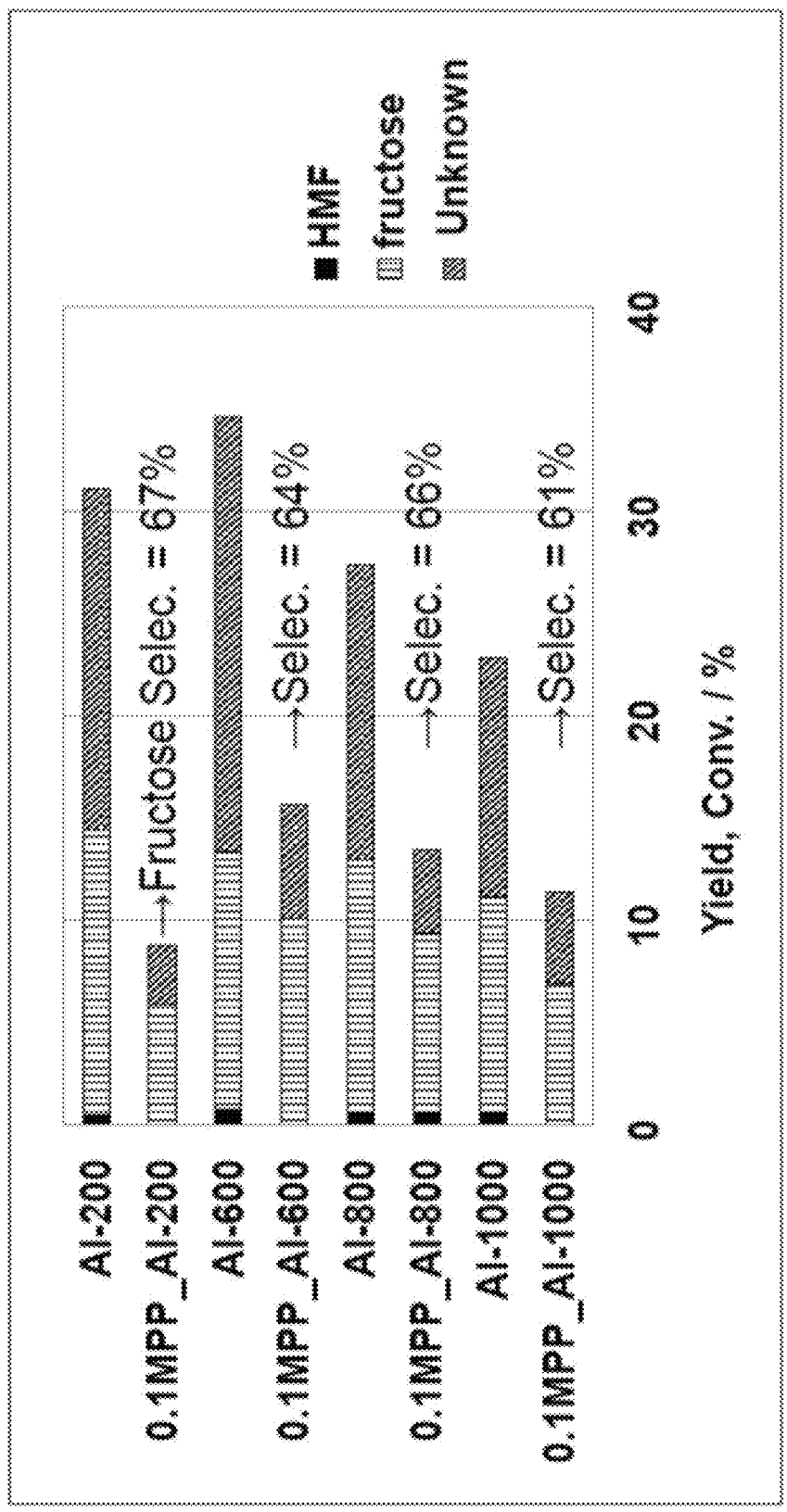
FIG. 4 illustrates results of a conversion reaction from glucose to fructose using phosphoric acid-treated aluminum oxide.

A reaction vessel was charged with 0.02 g of glucose, 2 g of water and 0.05 g of phosphoric acid-treated aluminum oxide, and the resultant was stirred at 120° C. for 2 hours. The thus obtained reaction solution was analyzed through high performance liquid chromatography. The result is illustrated in FIG. 4. It is noted that a result obtained in using, as a catalyst, aluminum oxide not subjected to the phosphoric acid treatment is also illustrated in FIG. 4. In this drawing, Al represents aluminum oxide, and a numerical value following Al indicates a calcination temperature. Besides, 0.1 MPP indicates the 0.1 M phosphoric acid treatment.

Figure 5:
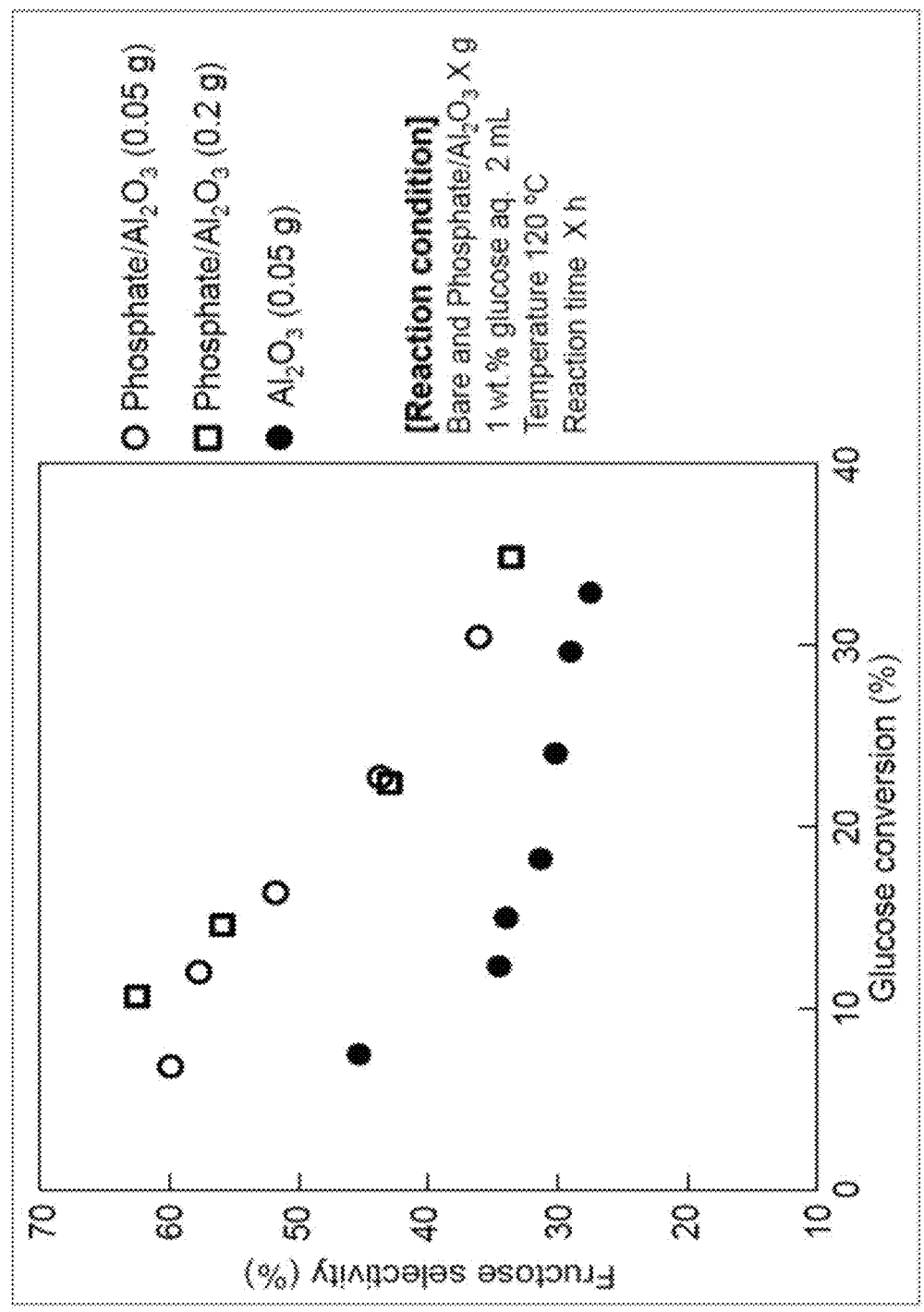
FIG. 5 illustrates a correlation between glucose conversion and fructose selectivity.

It is understood from FIG. 4 that a complicated side product (unknown) was remarkably reduced and fructose selectivity was remarkably improved in using the phosphoric acid-treated aluminum oxide as compared with those obtained in using the aluminum oxide not subjected to the phosphoric acid treatment. Besides, a correlation between glucose conversion and fructose selectivity is illustrated in FIG. 5. It is understood from FIG. 5 that the selectivity from glucose to fructose is remarkably improved by using the catalyst of the present invention.

Example 4

Figure 6:
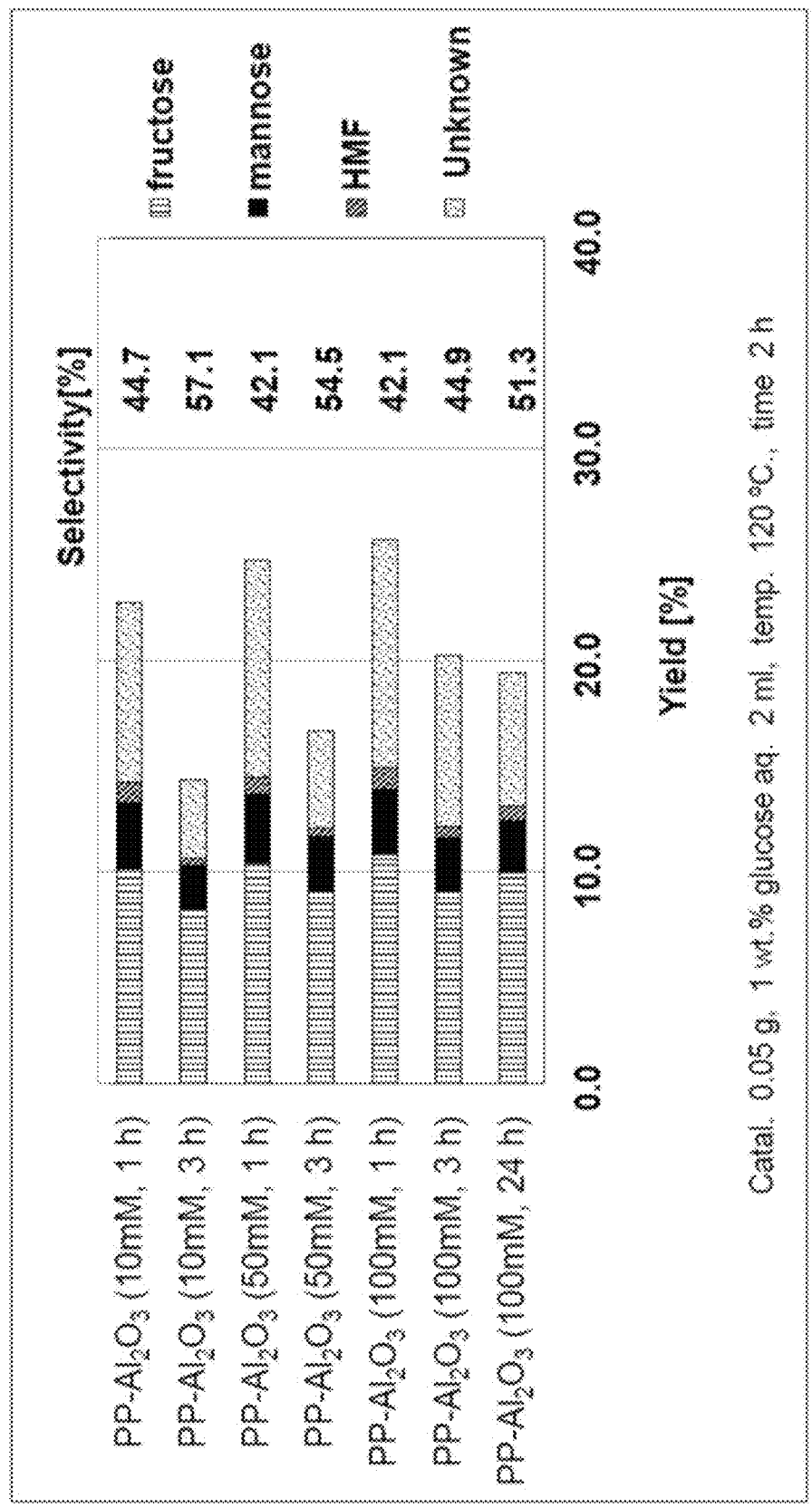
FIG. 6 illustrates results of a conversion reaction from glucose to fructose using phosphoric acid-treated aluminum oxide.

To a 1% by mass glucose aqueous solution, 0.05 g of phosphoric acid-treated aluminum oxide (which was obtained by stirring aluminum oxide calcined at 600° C. in a 10 to 100 mM phosphoric acid aqueous solution at 25° C. for 1 to 24 hours) was added, and the resultant was stirred at 120° C. for 2 hours. The thus obtained reaction solution was analyzed through the high performance liquid chromatography. Results are illustrated in FIG. 6. In this drawing, values in parentheses following PP—$Al_2O_3$ indicate conditions of the phosphoric acid treatment. In the drawing, selectivity refers to fructose selectivity.

It is understood from FIG. 6 that high fructose selectivity could be similarly attained even if the conditions of the phosphoric acid treatment for aluminum oxide were changed.

Example 5

Figure 7:
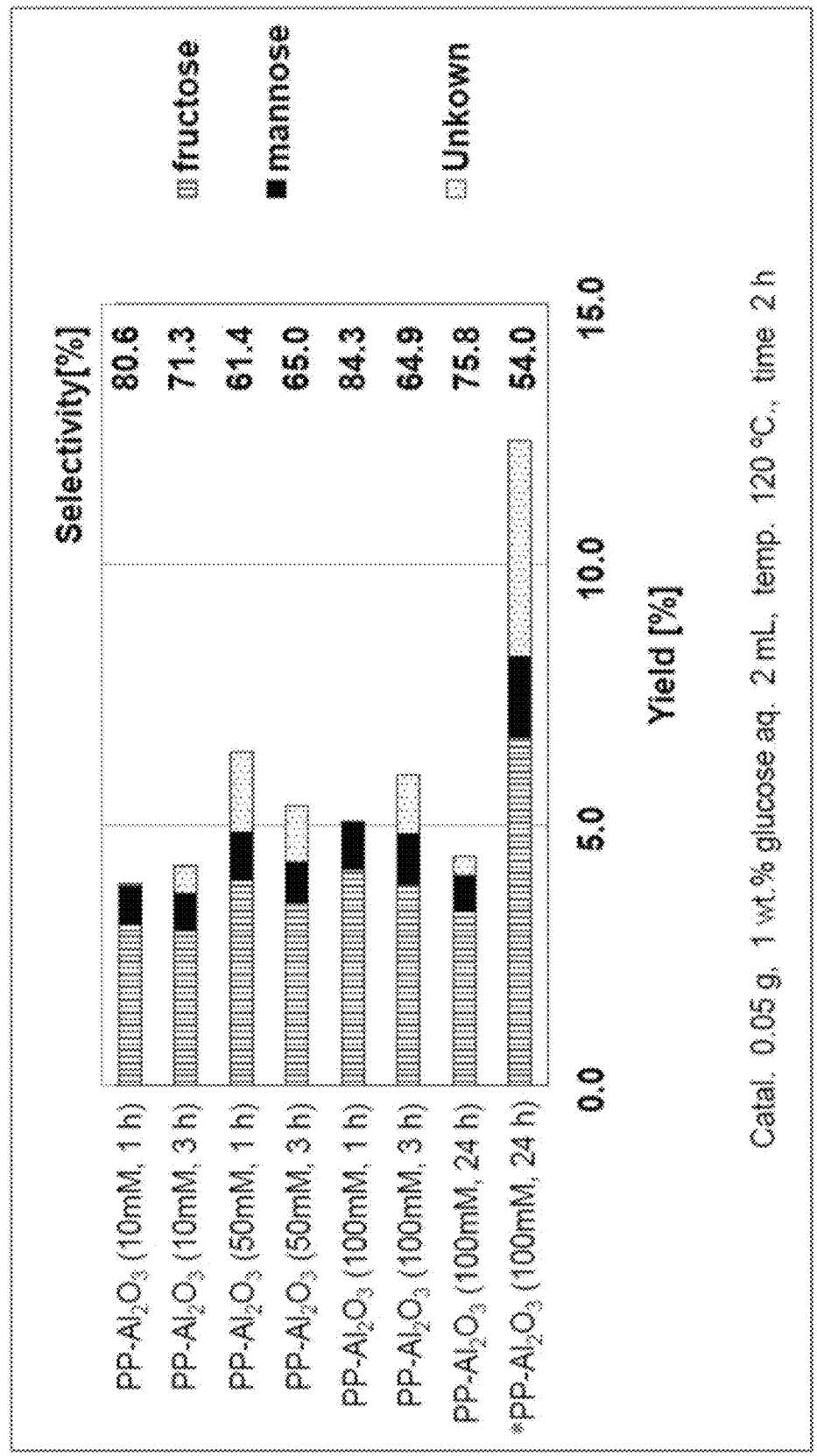
FIG. 7 illustrates results of a conversion reaction from glucose to fructose using phosphoric acid-treated aluminum oxide.

The reaction was performed in the same manner as in Example 4 except that the reaction temperature for glucose was changed from 120° C. to 100° C. The result is illustrated in FIG. 7. In this drawing, selectivity and symbols are defined in the same manner as in FIG. 6. It is noted that a sample with * was obtained with the reaction time for glucose set to 6 hours.

As is obvious from FIG. 7, high fructose selectivity was attained even when the reaction temperature for glucose was 100° C. in the same manner as when the reaction temperature was 120° C.

Example 6

To a 1% by mass glucose aqueous solution (2 mL), 0.05 g of gallium oxide, indium oxide (both of which are samples obtained through calcination at 400° C.) or a phosphoric acid-treated product (obtained by stirring each sample in a 100 mM phosphoric acid aqueous solution at 25° C. for 48 hours) was added, and the resultant was stirred at 120° C. for 2 hours. The thus obtained reaction solution was analyzed through the high performance liquid chromatography. The results are shown in Table 4.

TABLE 4

| Catalyst | Reaction time/h | Glucose conversion (%) | Fructose selectivity (%) |
| --- | --- | --- | --- |
| $Ga_2O_3$ | 2 | 10.3 | 35.3 |
| PP-$Ga_2O_3$ (0.1M) | 2 | 3.2 | 95.8 |
|  | 10 | 13.6 | 57.7 |
| $In_2O_3$ | 2 | 13.6 | 25.1 |
| PP-$In_2O_3$ (0.1M) | 10 | 2.4 | 78.9 |

It is understood from Table 4 that the fructose selectivity was remarkably improved in using the phosphoric acid-treated sample as compared with when the gallium oxide or the indium oxide not subjected to the phosphoric acid treatment was used.

The invention claimed is:

1. A method for selectively producing fructose as a produced product from glucose as a raw material, the method comprising:
    conducting a catalytic hydride isomerization reaction from glucose to fructose in the presence of a solid catalyst in water or in an aqueous solution,
    obtaining the produced product from the water or the aqueous solution,
    wherein the solid catalyst consists essentially of a Group 13 element oxide whose surface is bonded with a phosphoric acid to form a structure of —O—P(O)(OH)$_2$ with the Group 13 element oxide.

2. The method according to claim 1, wherein the produced product comprises fructose and mannose, and wherein the production of fructose from glucose has a selectivity ratio of at least 42.1%.

3. The method according to claim 1, wherein the Group 13 element oxide is at least one selected from the group consisting of aluminum oxide, gallium oxide, indium oxide and thallium oxide.

4. The method according to claim 1, wherein the Group 13 element oxide is obtained by treating an untreated Group 13 element oxide in a phosphoric acid aqueous solution at 50° C. or lower.

5. The method according to claim 1, wherein a Lewis acid is contained in the Group 13 element oxide whose surface is bonded with a phosphoric acid to form the structure of —O—P(O)(OH)$_2$ with the Group 13 element oxide, and wherein an amount of the Lewis acid in the Group 13 element oxide whose surface is bonded with a phosphoric acid to form the structure of —O—P(O)(OH)$_2$ with the Group 13 element oxide and which has been subjected to a phosphoric acid treatment is kept, in a state where the surface of the Group 13 element oxide is hydrated, at 80% or more of an amount of a Lewis acid in a Group 13 element oxide whose surface has not been subjected to a phosphoric acid treatment and has been dehydrated.

6. The method according to claim 1, wherein the surface of the Group 13 element oxide is bounded with the phosphoric acid in a phosphoric acid aqueous solution at 50° C. or lower to form the structure of —O—P(O)(OH)$_2$ with the Group 13 element oxide.

7. The method according to claim 1, wherein the Group 13 element oxide has a surface on which from 0.0001 to 0.003 mol % of the phosphoric acid is immobilized.

8. The method according to claim 1, wherein the surface of the Group 13 element oxide is bounded with the phosphoric acid in a phosphoric acid aqueous solution at 50° C. or lower to form the structure of —O—P(O)(OH)$_2$ with the Group 13 element oxide, and wherein the Group 13 element oxide has a surface on which from 0.0001 to 0.003 mol % of the phosphoric acid is immobilized.

* * * * *